United States Patent [19]

Hancock et al.

[11] Patent Number: 5,066,452
[45] Date of Patent: Nov. 19, 1991

[54] ULTRASONIC PROFILOMETRY SYSTEM FOR CONTROL ROD WEAR

[75] Inventors: Jimmy W. Hancock; Michael J. Kelly; Wayne M. Latham; Carlton E. Stinnett, all of Lynchburg, Va.

[73] Assignee: The Babcock & Wilcox Company, New Orleans, La.

[21] Appl. No.: 384,358

[22] Filed: Jul. 24, 1989

[51] Int. Cl.$^5$ .............................................. G21C 17/00
[52] U.S. Cl. .................................... 376/252; 376/245; 376/240; 376/249
[58] Field of Search ................ 376/245, 248, 249, 252, 376/240; 73/597, 632

[56] References Cited

U.S. PATENT DOCUMENTS

| | | | |
|---|---|---|---|
| 4,548,785 | 10/1985 | Richardson et al. | 376/249 |
| 4,649,749 | 5/1987 | Hazony | 73/629 |
| 4,741,878 | 5/1988 | Gebelin | 376/248 |
| 4,826,650 | 5/1989 | Richardson | 376/249 |
| 4,847,037 | 7/1989 | Scharpenberg | 376/245 |

Primary Examiner—Brooks H. Hunt
Assistant Examiner—Meena Chelliah
Attorney, Agent, or Firm—Robert J. Edwards; Vytas R. Matas; Eric Marich

[57] ABSTRACT

An apparatus and method for scanning the outer profile of control rods in a control rod assembly includes a plurality of rotatably mounted ultrasonic transducers which are mounted for rotation about the axis of at least some of the control rods in the assembly. The assembly is moved in a linear path parallel to the axis of the control rods, past the rotating transducers for scanning the surfaces of the control rods in helical paths. By distributing the transducers in a selected configuration, all control rods in the assembly can eventually be scanned.

20 Claims, 4 Drawing Sheets

ULTRASONIC PROFILOMETRY SYSTEM FOR CONTROL ROD WEAR

FIELD AND BACKGROUND OF THE INVENTION

The present invention relates in general to testing equipment and methods in nuclear power plants, and in particular to a new and useful method and apparatus for detecting and measuring wear on the control rods for the fuel assemblies for nuclear power plants.

More and more frequently, control rod assemblies (CRA) are being thought of as components of pressurized water reactor (PWR) systems which require periodic non-destructive evaluation (NDE). In light of recent observations of breach-of-cladding, plant owners are under increasing regulatory pressure to determine the condition of their control components and to insure that shutdown margins are within specifications. Damage mechanisms include vibratory contact with support or guide components and absorber swelling due to neutron irradiation. As a result of either gross diameter increase in the cladding or leeching of the poison from the cladding, the ability to scram the reactor could be jeopardized.

During the operation of a PWR, the control rods are suspended above the fuel assembly with the individual pins contained within the brazement guide structure. The tips of the pins are captured in guide tubes located in the fuel assemblies. Coolant flow through the guide tubes causes the pins to vibrate, and the resulting mechanical contact between the control rod pins and the support structure/fuel assembly guide tubes induces localized wear on the outside surface of the individual pins. There are at least two different flaw types in the CRA. The first flaw type is a large volume wear mark caused by contact with the guide tube nut. The second type of defect is a small volume, axial groove caused by contact with the brazement support structure above the fuel assembly.

In the past, inspection of control rods, the primary component of rod cluster control assemblies (RCCAs) in pressurized water reactors, has been performed non-destructively, using various eddy current techniques. These eddy current techniques have been used to look for and measure cracks and wear marks that, if large enough, could render an RCCA unusable. The use of eddy current coils has been successful in determining the existence of a breach in cladding or the amount of material left on a control rod. In some situations, measuring the percent of material remaining has provided sufficient information for determining the useability of a control rod. In fact, pass/fail criteria has largely been based upon the kind of data (i.e. location, quantity and accuracy of data points) collected by eddy current inspection equipments.

Inherent in the making of eddy current measurements and especially in the interpretation of the measurements is the problem of material variability. Because eddy current measurements are based on the electrical properties of the material of which the control rods are made, a control rod calibration standard must be produced to replicate the actual control rod and damage mechanisms as closely as possible. Any difference in material or defect geometry has the potential to be a source of error in data collected on actual control rods. If a very precise method of measurement that is not dependent upon material properties could be integrated in a system to inspect control rods, the accuracy of measurement data could be improved.

SUMMARY OF THE INVENTION

The present invention utilizes an ultrasonic non-destructive technique to detect wear on the control rods. The system is comprised of a rotating UT transducer mounting fixture which rests on a storage rack in the spent fuel pool of a nuclear power plant. This fixture houses and rotates a series of transducers while the control rod cluster is run through the fixture. The transducers maintain a constant distance from the control rods at all times as the transducers float to preserve transducer standoff. The system uses high frequency focussed transducers, multichannel ultrasonic thickness gauging instrumentation, a probe/electronics switching network, and a calibration standard.

A conventional pulse-echo ultrasonic technique is used by the invention in conjunction with an immersion transducer to measure water path. Taking advantage of the velocity (longitudinal) difference between steel and water, a water path measurement provides a profile of the outside surface of the control rod by gauging the spacing between transducer and the test surface. This ultrasonic profilometry system uses the multichannel ultrasonic thickness gauge and multiple test stations to examine several control rods simultaneously. The transducers are rotated continuously around the control rods, maintaining constant spacing between the transducer and the individual control rods. The control rods are raised and lowered through the inspection fixture by the existing refueling mast in the plant, effecting a helical scan which provides maximum coverage. Both the pulse voltage and reflected signal are transmitted through slip rings, and the resulting data indicative of rod profile are recorded on computer-based oscillographic strip chart via the analog output of the thickness gauge.

This ultrasonic technique has advantages over an electromagnetic method for this particular application for several reasons. It is not hindered by variations in the electrical properties of coatings applied to the outside surface of the control rods; it is unaffected by the presence of conductive material inside the control rods; and it is not dependent on representative calibration standard flaw geometry for sizing accuracy.

The system can inspect 25% of the rods during one pass of the rod cluster control assembly (RCCA) through the UT transducer mounting fixture. To inspect the remaining rods the RCCA is removed from the fixture and rotated 90°. The RCCA is then lowered back into the fixture and the rods inspected. This is repeated until all control rods have been inspected.

The entire process is supported by any additional support tooling which itself, does not form a part of this invention.

On-site activities can be performed off the side of the spent fuel pool or off a bridge in the spent fuel pool.

Accordingly, an objective of the present invention is to provide an apparatus and method for scanning the outer profile of control rods, in particular, for nuclear fuel assemblies, comprising an ultrasonic transducer for sending an ultrasonic beam to, and for receiving an ultrasonic echo signal from the surface of a control rod, rotation means connected to the ultrasonic transducer for rotating the transducer around the axis of the control rod, and control rod translation means for translating the control rod with respect to the transducer, parallel to the axis of the control rod, for scanning the surface of the control rod along its length.

A further object of the present invention is to provide an apparatus which can be used to measure the outer profile of control rods, in particular for detecting wear and surface defects, which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
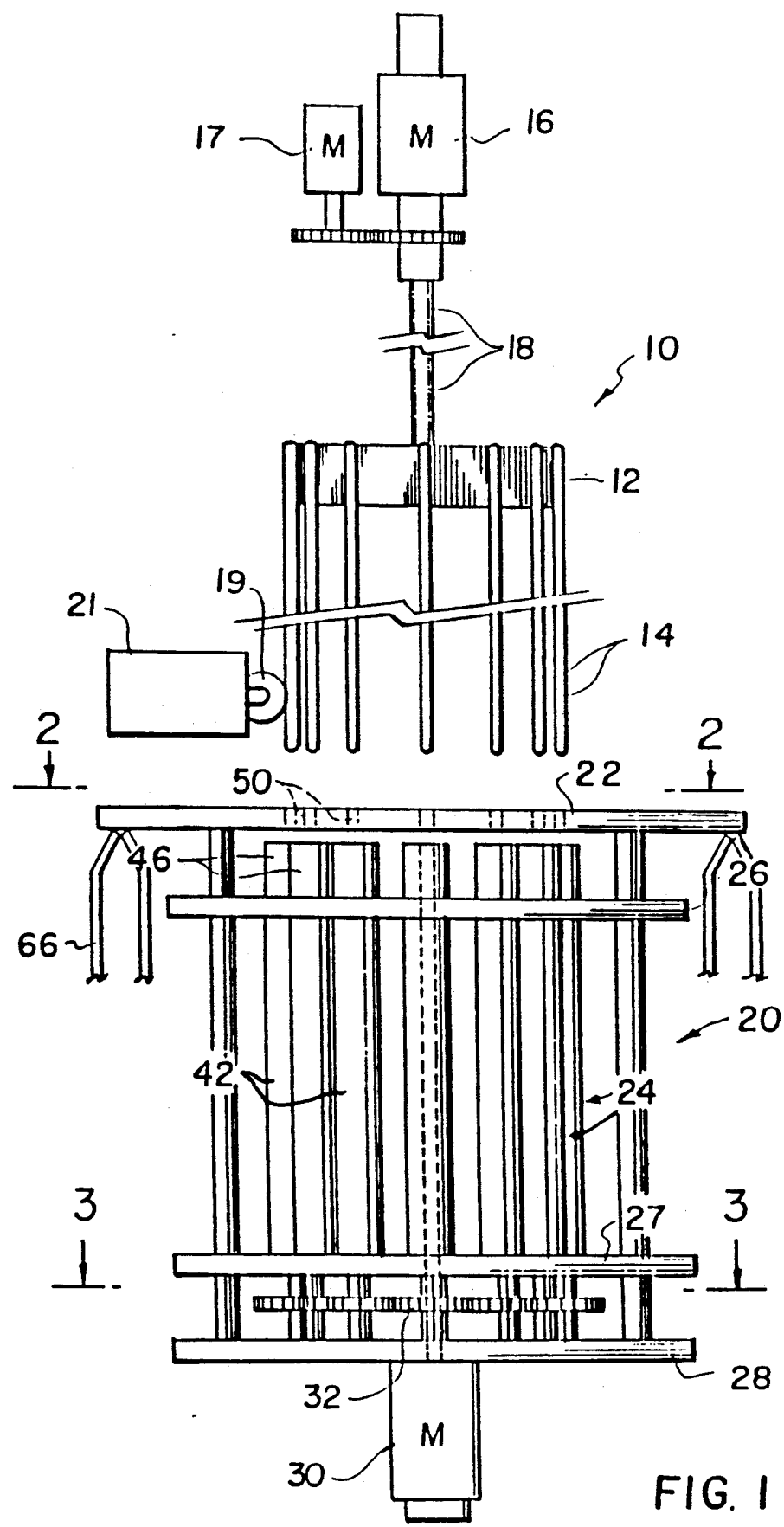
FIG. 1 is a side elevational view of an apparatus for scanning and detecting the outer profile of control rods, in accordance with the present invention.

Referring to the drawings in particular, the invention embodied in FIG. 1 comprises an apparatus for scanning and detecting the profile of control rods 14 which are connected by a spider 12 into a control rod assembly generally designated 10. As is conventional, control rod assembly 10 may be driven parallel to the axis of the control rods 14, by a control rod drive unit 16. Control rod drive unit 16 may include a roller assembly which engages a lead screw assembly 18 to move spider 12 in a direction parallel to the axis of rods 14.

Control rod assembly 10 is also provided with a rotation driver schematically shown at 17 for rotating the assembly about the axis of lead screw 18.

The ultrasonic profilometry assembly of the present invention, generally designated 20, is mounted to an assembly support plate 22, which may for example rest upon the top of a spent fuel pool rack in a nuclear power plant shown schematically at 66. A refueling mast may be used as the assembly drive unit 16 and lead screw 18.

To scan the outer profile of control rods 14, the control rod assembly is lowered through entry guides 50 in plate 22 into a set of ultrasonic transducer modules 24 which are mounted to module support plate 26 carried under plate 22.

As will be explained later, each module 24 contains a rotatably mounted ultrasonic transducer.

The ultrasonic transducer in modules 24 are each rotated by a drive motor 30 mounted to a motor support plate 28 which is carried by an idler support plate 27.

Figure 2:
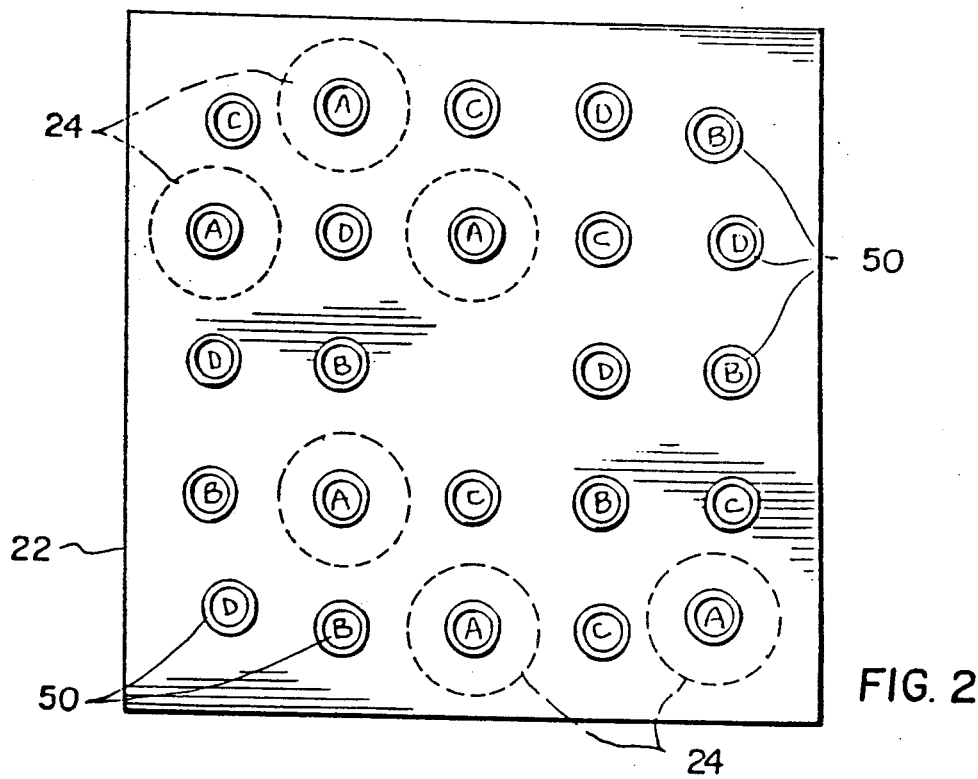
FIG. 2 is a top plan view taken along line 2—2 of FIG. 1.

FIG. 2 shows the configuration of entry guides 50 in plate 22 which corresponds to the configuration of control rods 14 in spider 12. The position of six modules 24 is shown in FIG. 2 which service six control rods at positions A.

In accordance with the invention, when drive unit 16 lowers control rods 14 into plate 22, half of the modules 24 are operated to scan the outer surface of the control rods. When the control rods are raised by drive unit 16, the other half of the modules scan an additional three control rods.

Due to the relative rotation and translation between the transducers and control rods, a helical path on the outer surface of each control rod is scanned. With a rotational speed of 600 rpm, and an axial speed of one inch per second, a helical pitch of 0.100 inches is obtained.

The vertical position of the control rod assembly is recorded continuously. This can be achieved, for example, using a wheel shown at 19 in FIG. 1 which is connected to an encoder 21 which feeds out the vertical position of the control rod assembly at any point during the process. A release spring can be engaged to the wheel 19 for gently urging it against the control rod. Two O-rings are advantageously connected to the wheel around the circumference thereof and engaged against the control rod to avoid damage to the control rod and to promote tracking by centering the wheel on the control rod. Encoder 21 may advantageously be in the form of a proximity switch which is mounted parallel to the wheel axis and which is aimed at holes in the wheel which are circumferentially spaced around the wheel axis. The switch provides a signal to a control computer which can be used in conjunction with the apparatus of the invention. Each time a hole passes the switch, a signal is sent to the computer. The distance between each signal corresponds to the linear distance traveled by the control rod assembly.

Figure 4:
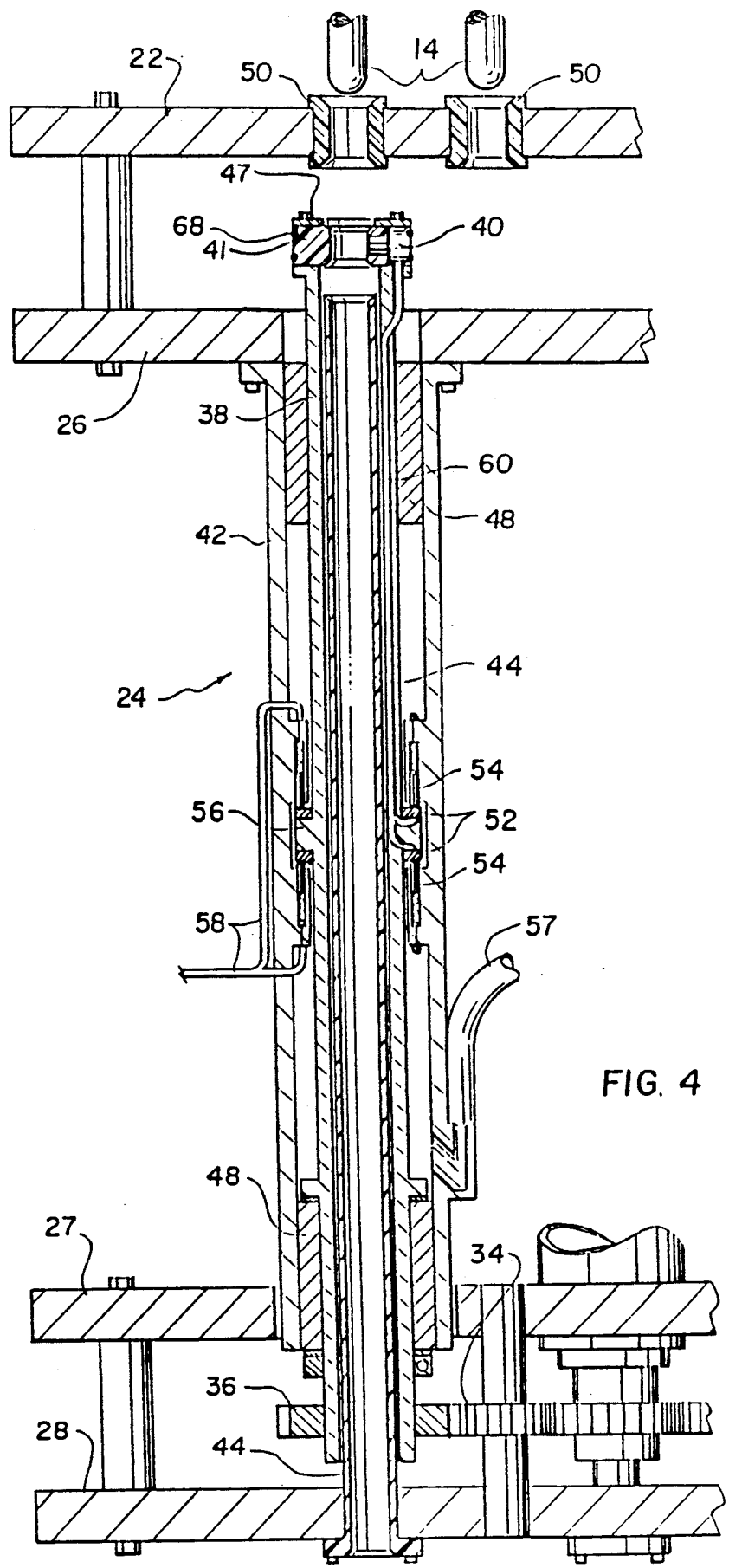
FIG. 4 is a vertical sectional view, on an enlarged scale, taken along line 4—4 of FIG. 3.

As shown in FIG. 4, each transducer module 24 comprises a fixed outer housing 42 which is mounted to plate 26. A transducer drive tube 38 is mounted between slide bushings 48 that are fixed to housing 42, for rotation about the axis of one control rod 14.

An ultrasonic transducer 40 is fixed in a transducer holder 41. The transducer holder 41 is slidably mounted to the top of the transducer drive tube 38, and is confined to move in a plane perpendicular to the axis of the control rod. The transducer holder comprises an assemblage of two or more parts, constrained in the axial direction by the top of transducer drive tube 38 and cap 47 and in the radial direction by elastic rings 68 to ride on the outside surface of the control rod. The capacity of the transducer holder 41 to slide or "float" in a plane perpendicular to the axis of the control rod allows the transducer holder to stay in contact with the control rod without the axis of the transducer drive tube being exactly coincident with the axis of control rod 14. The amount of misalignment is governed by the clearance in guide 50 and is smaller than the amount of float in the transducer holder mounting.

Figure 5:
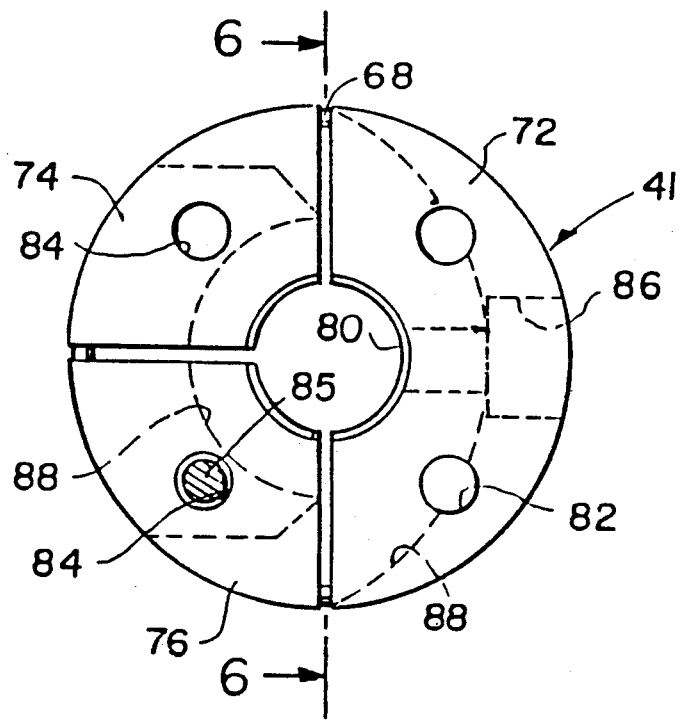
FIG. 5 is a top plan view of a transducer holder of the invention.
Figure 6:
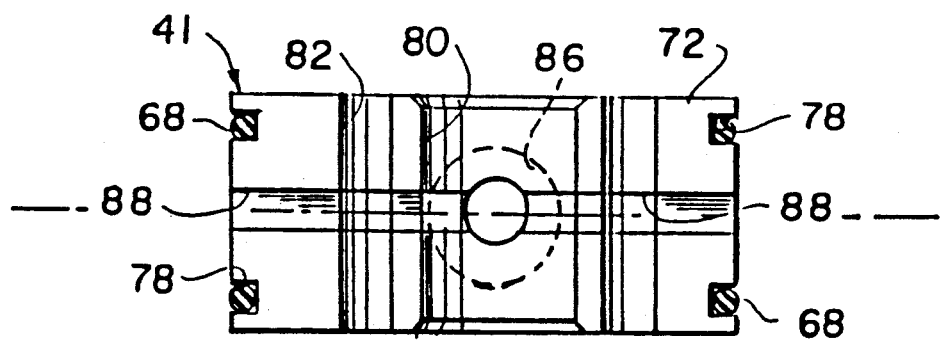
FIG. 6 is a sectional view taken along line 6—6 of FIG. 5.

Turning to FIGS. 5 and 6, the transducer holder 41 is made of three plastic parts 72, 74 and 76 which are originally formed from one generally cylindrical piece of plastic and cut into the three parts. The three parts are held together by O-rings 68 which lie in grooves 78 above and below the axis of symmetry. O-rings 68 produce a gentle inward clamping against the control rod which is guided within passage 80 defined at the center of the holder. Two holes 82 are defined in holder part 72 and one hole 84 are defined in each of the other holder parts 74 and 76. The diameter of the holes 82 and 84 are selected to be approximately 30 to 40 thousandths of an inch larger than the diameter of shoulder bolts 85 to be received by the holes for holding the cap 47 in place over the holder 41. This permits the radial movement of the holder parts 72, 74 and 76, to permit these parts to "float" as the control rod passes with respect to passage 80. O-rings 68 exert a gentle clamping force which allows the transducer holder 41 to adjust to changes in the profile of the control rod. Not enough pressure is exerted to distort any part of the holder or rod which would produce false readings.

A blind bore 86 is machined in part 72 for receiving the body of transducer 40. Blind bore 86 communicates with an inner groove 88 having a generally C-shaped configuration and passing through each of the parts of the holder 41. Groove 88 is important as it provides a water path between the ultrasonic transducer and the control rod being inspected. Experiments indicate that the invention operates correctly with the groove but does not operate correctly without this groove. It is believed that the groove prevents cavitation created when the transducer is rotated around the control rod at 600 rpm.

In addition to the plastic holder 41, the guide sleeve 44 and the guide 50 may also be made of plastic material to withstand the environment and to avoid any contact between the control rods and metal.

An inner guide sleeve 44 which is fixed to motor support plate 28 and extends into the center of drive tube 38, further helps center the control rod 14 within the transducer module 24.

Good results have been achieved according to the present invention by utilizing a 20 MHz spherically focused transducer 40 with a focal length of 0.25 inches. The beam diameter at the focal point of this transducer is approximately 0.010 inches which allows for the detection of very narrow flaws in the outer surface of the control rod 14. A precision ultrasonic thickness gauge (not shown) is used in conjunction with each transducer. The signal from each transducer is gated and any change in position of this signal caused by a wear mark is seen as a change of voltage from the analog output of the gauge. Data from each thickness gauge is acquired at 1,200 Hz by a computer based oscillographic data acquisition system which provides a real time display of the output for each thickness gauge, and a data storage on a computer hard disk.

An ultrasonic transducer which has been used to practice the present invention is the Panametrics Part No. V3527. A Panametrics Part No. 5215-BW1 Ultrasonic Thickness Gauge has been used in conjunction with the Panametrics transducer. The thickness gauge has been modified to extend its band width to include a frequency response up to 30 MHz, to provide better compatibility with the 20 MHz transducer. The three transducers which are used in the three modules of the present invention simultaneously, are also synchronized with one transducer acting as a master and the other two acting as slaves, in order to synchronize pulses and avoid crosstalk.

The foregoing is useful for example, to determine whether large volume wear marks caused by contact with the guide tube nut, or small volume defects such as axial grooves caused by contact with the brazement support structure above the fuel assembly, are present. The skilled artisan will understand that a broad range of sonic frequencies can be utilized depending on the type of defect being measured. Typically, for the type of defects specified above, a range of 10–30 MHz would be reasonable.

The system's circumferential resolution of 0.010 inches is equal to 120 data points per transducer revolution or 1,200 data points per second, per rod. A hard disk has sufficient capacity to store the data from the inspection of at least two complete RCCAs (48 rods) with 100% inspection. After inspection, data acquired in accordance with the present invention is transferred to a streaming tape or other form of permanent storage.

In order to scan all rods in a control rod assembly, after two linear passes of the control rod assembly which detects a profile of rods shown at position A in FIG. 2, the assembly is withdrawn from plate 22 and rotated by rotation means 17 through 90°. This brings a new set of six control rods into position B of FIG. 2, into alignment with the six modules 24.

This operation can be repeated by rotating the assembly through another 90° to scan rods in position C. A further rotation of 90° for the control rod assembly brings rods in position D, into place for scanning. In this way, all rods in a single control rod assembly can be scanned by the single set of six modules. Other configurations for the control rods and modules can be utilized.

Figure 3:
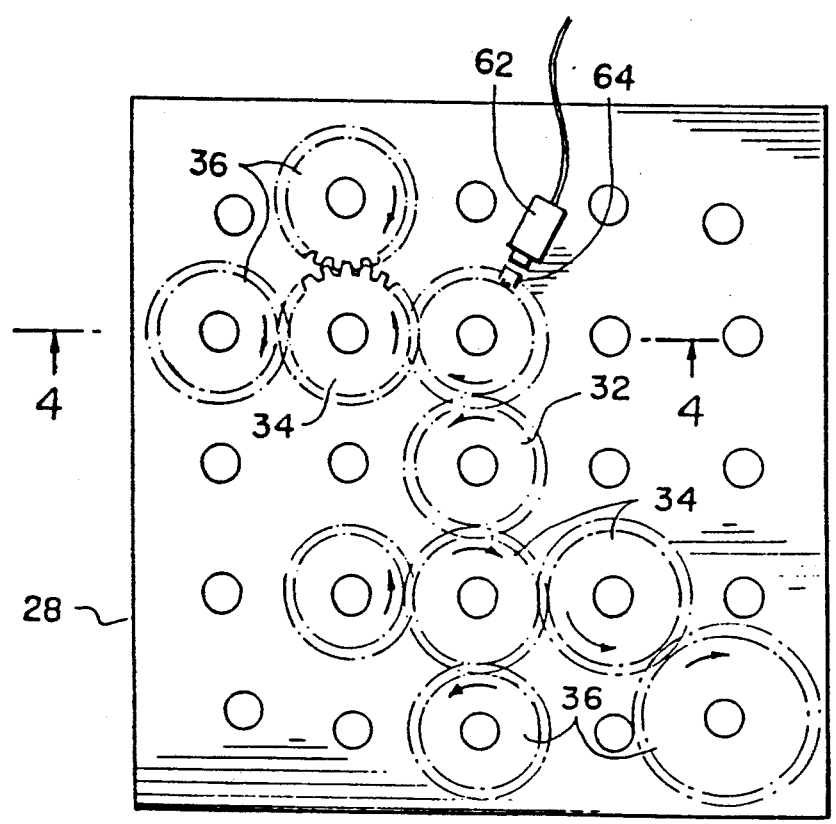
FIG. 3 is a sectional view taken along line 3—3 of FIG. 1.

Turning now to FIG. 3, all six transducers and the six modules can be rotated using a single drive motor 30 which is connected to a drive spur gear 32. Spur gear 32 is engaged with a combination of idler gears 34 and module gears 36. Each module gear 36 is connected to its own transducer drive tube 38 as shown in FIG. 4. In this way all transducers can be rotated at the same time.

To establish a correlation between data points and the circumferential position of each transducer, a further proximity switch 62 is mounted on plate 28 which cooperates with a pin 64 on one of the gears 36. This provides a signal upon each complete revolution of the transducers, to establish a reference position for the transducers.

The transducers are submerged in water so that a water path measurement is obtained using the ultrasonic transducers.

Drive motor 30 may advantageously be a submerseable DC motor.

Alternatively, other types of motors, such as miniature air motors, may be used. Further, transmission means other than spur gears, may be utilized, such as stainless steel chains or the like.

To transmit the signal from transducer 40 to external instrumentation, a pair of wires 60 is connected between transducer 40 and a pair of slip rings 52 which are mounted on an electrically insulated collar 56 fixed to drive tube 38.

Spring loaded brushes 54 mounted to fixed housing 42 are connected to wires 58 for conveying the signal away from each module.

A supply of water can be provided to the interior of each module for insulation or flushing through a conduit 57.

The slip ring assembly should be operated in a non-conductive environment. Because the spent fuel pool water can be conductive, the slip ring assembly can be insulated from the pool water by deionized water supplied through conduit 57. A continuous supply of water through conduit 57 at increased pressure excludes pool water from the slip ring assembly.

Advantages of the present invention include the fact that the ultrasonic system is highly sensitive and accurate for small volume defects, particularly when compared to previous eddy current methods. The invention is inherently able to provide better profilometry information than an eddy current system because of the large number of points measured upon each revolution of the transducer. With better profilometry data, a better assessment of control rod wear, and the mechanisms for causing such wear, can be made. The invention does not depend on representative calibration standard flaw geometry for accurate depth estimation as in the eddy current method because absolute wear depth is measured as a change in water path. The system is also not encumbered by material property variations, variations in cladding thickness, or by conductivity variations in the cladding material. In addition, the measurements are not affected by the presence of conductive absorber materials such as silver-indium-cadmium, or hafnium.

While a specific embodiment of the invention has been shown and described in detail to illustrate the application of the principles of the invention, it will be understood that the invention may be embodied otherwise without departing from such principles.

What is claimed is:

1. An apparatus for scanning the outer profile of control rods, comprising:
    a module support positioned at a fixed location with respect to a control rod to be scanned, a transducer drive tube mounted for rotation about the axis of a control rod for receiving a control rod therein, a transducer holder connected to the transducer drive tube carrying ultrasonic transducer means facing an interior of said transducer drive tube, for sending an ultrasonic beam to and receiving ultrasonic echo energy from the surface of the control rod, said holder having at least one part for carrying said ultrasonic transducer means which is mounted for limited radial movement with respect to said transducer drive tube;
    rotation means, mounted to said module support and engaged with said transducer drive tube for rotating said transducer drive tube and said ultrasonic transducer means around the axis of the control rod; and
    translation means for translating the control rod with respect to said ultrasonic transducer means, in a direction parallel to the axis of the control rod, for scanning the surface of the control rod along a helical path.

2. An apparatus according to claim 1 wherein said rotation means comprises a motor connected to said module support and a drive transmission operatively connected between said motor and said tube for rotating said tube.

3. An apparatus according to claim 1 wherein said module support comprises a pair of spaced apart plates, a fixed housing connecting between said plates for containing said transducer drive tube, and slip ring means connected to said transducer and operatively connected between said transducer support tube and said fixed housing for transmitting signals to and from said transducer from outside said fixed housing.

4. An apparatus according to claim 1 wherein said module support includes a mounting plate and a control rod guide tube connected to said mounting plate and extending axially in said transducer drive tube for guiding a control rod in said transducer support tube.

5. An apparatus according to claim 1 wherein said module support includes a guide plate having a configuration of guides corresponding to a configuration of a plurality of control rods in a control rod assembly to be scanned, said translation means comprising drive means for driving the configuration of control rods into guides of said plate, and a plurality of transducer drive tubes each carrying a separate ultrasonic transducer and distributed in a second configuration for servicing a selected number of control rods in said first mentioned configuration, said first mentioned and second configurations being selected so that with relative rotation between the control rod assembly and said module support, all control rods of the assembly are serviced by said plurality of transducers.

6. An apparatus according to claim 1 including a passage defined through said holder having a diameter for closely receiving a control rod therethrough.

7. An apparatus according to claim 6 including a groove defined in said holder for receiving water, said transducer having a sensing end communication with said groove.

8. An apparatus according to claim 7 wherein said holder is generally cylindrical in shape and comprises a first part for carrying said transducer and for carrying one side of said passage and at least one additional part for carrying an additional side of said passage.

9. An apparatus according to claim 8 including resilient ring means engaged around said parts of said holder for resiliently holding said holder passage against a control rod.

10. A method of scanning the outer profile of control rods, comprising:
    providing an ultrasonic transducer on a holder having a passage for receiving a control rod, and resiliently urging the holder against the control rod for centering the holder with respect to the control rod;
    rotating the ultrasonic transducer about an axis of the control rod to be scanned;
    translating the control rod parallel to its axis and with respect to the transducer for defining a helical path which is followed by the transducer over the surface of the control rod;
    emitting ultrasonic energy to the surface of the control rod as the transducer rotates and as the control rod is translated with respect to the transducer; and
    receiving ultrasonic echo energy from the surface of the control rod which contains information concerning the distance between the transducer and the surface of the control rod which in turn indicates the profile of the surface.

11. A method according to claim 10 including scanning a plurality of controls rods in a configuration of control rods, mounting a plurality of ultrasonic transducers to a module support, each for rotation around the axis of a separate control rod in the configuration, the transducers being distributed in a subconfiguration which is selected so that with rotation between the control rod configuration and the module support, all control rods can be serviced by the subconfiguration of transducers.

12. An apparatus according to claim 2, wherein said motor is a submerseable DC motor.

13. An apparatus according to claim 2, wherein said motor is a miniature air motor.

14. An apparatus according to claim 2, wherein said drive transmission comprises a drive spur gear connected to said motor and operatively engaged with a combination of idler gears and module gears, said module gears being connected to said transducer drive tube.

15. An apparatus according to claim 2, wherein said drive transmission comprises stainless steel chains connected to said motor and to said transducer drive tube.

16. An apparatus according to claim 3, further including a conduit connected to said transducer support tube for providing a supply of water to the interior of each module for insulation or flushing said slip ring assembly.

17. An apparatus according to claim 16, wherein said supply of water is deionized water to provide a non-conductive environment for said slip ring assembly.

18. An apparatus according to claim 1, wherein said transducer holder is made of plastic material to withstand the environment and to avoid any contact between the control rods and metal.

19. An apparatus according to claim 4, wherein said control rod guide tube is made of plastic material to withstand the environment and to avoid any contact between the control rods and metal.

20. An apparatus according to claim 5, wherein said guides are made of plastic material to withstand the environment and to avoid any contact between the control rods and metal.

* * * * *